(12) United States Patent
Ainger et al.

(10) Patent No.: US 12,403,080 B2
(45) Date of Patent: Sep. 2, 2025

(54) PERSONAL CARE COMPOSITION AND METHODS

(71) Applicant: Conopco, Inc., Englewood Cliffs, NJ (US)

(72) Inventors: John Nicholas Ainger, Wallasey (GB); Luisa Zoe Collins, Chester (GB); Joanna Susan Sawson, Bebington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 94 days.

(21) Appl. No.: 17/909,725

(22) PCT Filed: Jan. 6, 2021

(86) PCT No.: PCT/EP2021/050127
§ 371 (c)(1),
(2) Date: Sep. 6, 2022

(87) PCT Pub. No.: WO2021/175499
PCT Pub. Date: Sep. 10, 2021

(65) Prior Publication Data
US 2024/0216244 A1 Jul. 4, 2024

(30) Foreign Application Priority Data
Mar. 6, 2020 (EP) .................................. 201614187

(51) Int. Cl.
| | |
|---|---|
| A61Q 5/02 | (2006.01) |
| A61K 8/36 | (2006.01) |
| A61K 8/44 | (2006.01) |
| A61K 8/46 | (2006.01) |
| A61K 8/49 | (2006.01) |
| A61K 8/92 | (2006.01) |
| A61Q 5/00 | (2006.01) |

(52) U.S. Cl.
CPC ............ *A61K 8/4926* (2013.01); *A61K 8/361* (2013.01); *A61K 8/442* (2013.01); *A61K 8/463* (2013.01); *A61K 8/922* (2013.01); *A61Q 5/006* (2013.01); *A61Q 5/02* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 3,958,581 A | 5/1976 | Abegg et al. | |
| 3,962,418 A | 6/1976 | Birkofer | |
| 4,009,256 A | 2/1977 | Nowak, Jr. et al. | |
| 5,194,639 A | 3/1993 | Connor et al. | |
| 2002/0035161 A1 | 3/2002 | Segura et al. | |
| 2002/0172648 A1 | 11/2002 | Hehner et al. | |
| 2003/0108507 A1 | 6/2003 | Clipson et al. | |
| 2004/0234483 A1 | 11/2004 | Peffly et al. | |
| 2006/0120988 A1 | 6/2006 | Bailey et al. | |
| 2014/0348886 A1 | 11/2014 | Johnson et al. | |
| 2015/0216774 A1* | 8/2015 | Yu ......................... A61K 8/817 132/202 |
| 2019/0142800 A1 | 5/2019 | Ghosh et al. | |
| 2019/0184209 A1 | 6/2019 | Schroeder et al. | |
| 2019/0262249 A1 | 8/2019 | Guskey et al. | |
| 2019/0328647 A1 | 10/2019 | Chang et al. | |

FOREIGN PATENT DOCUMENTS

| | | | |
|---|---|---|---|
| CN | 109152708 | 1/2019 | |
| CN | 109328054 | 2/2019 | |
| DE | 102017223063 | 6/2019 | |
| EP | 1238645 | 9/2002 | |
| EP | 3695825 | 8/2020 | |
| JP | 2006206582 | 8/2006 | |
| JP | 2010275198 | 12/2010 | |
| WO | WO9206154 | 4/1992 | |
| WO | WO9522311 | 8/1995 | |
| WO | WO9631188 | 10/1996 | |
| WO | WO03094874 | 11/2003 | |
| WO | WO2004056329 | 7/2004 | |
| WO | WO2014195872 | 12/2014 | |
| WO | WO-2014195872 A1 * | 12/2014 | ............. A01N 25/12 |
| WO | WO2016058836 | 4/2016 | |
| WO | WO2017202651 | 11/2017 | |
| WO | WO2017216722 | 12/2017 | |
| WO | WO2018007332 | 1/2018 | |

OTHER PUBLICATIONS

IPRP in PCTEP2021050127; Jun. 20, 2022; World Intellectual Property Org. (WIPO).
Search Report and Written Opinion in EP20161418.7; Jul. 28, 2020; European Patent Office (EPO).
Search report and Written Opinion in PCTEP2021050127; Apr. 20, 2021; World Intellectual Property Org. (WIPO).
Written Opinion 2 in PCTEP2021050127; Feb. 11, 2022; World Intellectual Property Org. (WIPO).

\* cited by examiner

*Primary Examiner* — Ali Soroush
*Assistant Examiner* — Samantha J Knight
(74) *Attorney, Agent, or Firm* — Byrne Poh LLP; Nina R. Horan

(57) ABSTRACT

A personal cleansing composition comprising: i) a cleansing surfactant comprising an amphoteric surfactant and an anionic surfactant which if ethoxylated has a degree of ethoxylation of less than 3, in which the ratio of anionic surfactant to amphoteric surfactant is less than 5:1; ii) an oil phase comprising at least one triglyceride oil; iii) an aliphatic fatty acid or salt thereof having a carbon chain length from $C_4$ to $C_{10}$; and iv) a piroctone compound; in which the composition has a pH at 20° C. of 16 or less and the weight ratio of aliphatic fatty acid to triglyceride oil is from 1:2 to 5:1.

20 Claims, No Drawings

PERSONAL CARE COMPOSITION AND METHODS

CROSS-REFERENCE TO RELATED APPLICATIONS

This application is a U.S. national phase application under 35 U.S.C. § 371 of International Application No. PCT/EP2021/050127, filed on Jan. 6, 2021, which claims priority to EP patent application No. 20161418.7, filed Mar. 6, 2020, the entire disclosures of which are incorporated herein by reference in their entireties, for any and all purposes.

FIELD OF THE INVENTION

The present invention relates to a hair treatment composition, particularly an anti-dandruff shampoo composition.

BACKGROUND OF THE INVENTION

Dandruff is a problem affecting many globally. The condition is manifested by the shedding of clumps of dead skin cells from the scalp, these are white in colour and provide an aesthetically displeasing appearance. A factor that contributes to dandruff are certain members of the *Malassezia* yeasts. To combat these years, hair treatment compositions are developed including various actives for their antidandruff effectiveness. Piroctone compound such as piroctone olamine is one such active.

A common problem with piroctone compound is that deposition of the active onto the desired surface during wash process is minimum. The desired surface is typically scalp and/or hair. For example, piroctone compound such as piroctone olamine is usually soluble in surfactants of the cleansing phase comprised in a hair treatment composition. During the excessive rinsing process, the majority of piroctone is likely to be washed away together with the surfactants. Poor deposition is correlated with low antidandruff activity, thus little mitigation of the ill-effects of dandruff. To date, there are attempts to offset this drawback by increasing the level of piroctone olamine in hair treatment composition. Such approach causes a variety of issues such as increased costs, potential instability of the formulation and potential adverse effect to hair sensory. Hence it is not an approach favoured by the industry.

US2002/0035161A1 describes a cosmetic/pharmaceutical oil-in-water emulsion including a discontinuous fatty phase dispersed in a continuous aqueous phase and comprising an effective amount of at least one biologically active agent (A) and an effect amount of an emulsifying system (B) therefore, said at least one biologically active (A) being non-solubilized therein in micronized particulate state, at least 80%, numerically, of said micronized particles having diameters ranging from 1 to 10 µm and at least 50%, also numerically, having diameters of less than 5 µm.

Co-pending European application number discloses enhanced deposition of Octopirox in a hair care composition containing a cleansing surfactant comprising an amphoteric surfactant and an ethoxylated anionic surfactant at a ratio from 2:1 to 6:1.

Improved deposition of Octopirox in a composition comprising polyquaternium 6 is disclosed in Co-pending European application 11988726.4.

Despite all the prior art, there remains a need to improve the deposition of piroctone compounds, especially piroctone acid or piroctone olamine, onto the surface of scalp and/or hair during washing process. There also remains a further need to improve the deposition onto said surface without adverse side effects to sensory, formulation rheology and conditioning performance.

DESCRIPTION OF THE INVENTION

The present invention relates to a personal cleansing composition comprising
i) a cleansing surfactant comprising an amphoteric surfactant and an anionic surfactant which if ethoxylated has a degree of ethoxylation of less than 3, in which the ratio of anionic surfactant to amphoteric surfactant is less than 5:1;
ii) an oil phase comprising at least one liquid hydrocarbon triglyceride oil;
iii) an aliphatic fatty acid or salt thereof having a carbon chain length from $C_4$ to $C_{10}$; and
iv) a piroctone compound;
in which the composition has a pH at 20° C. of less 6 or less, and the weight ratio of aliphatic fatty acid to triglyceride oil is from 1:2 to 5:1.

The invention also relates to a non-therapeutic method of treating hair or the scalp, comprising application of the personal care composition described above.

The invention further relates to a composition described above use in a method to mitigate dandruff.

For the avoidance of doubt, any feature of one aspect of the present invention may be utilised in any other aspect of the invention. Any feature described as 'preferred' should be understood to be particularly preferred in combination with a further preferred feature or features. Herein, any feature of a particular embodiment may be utilized in any other embodiment of the invention. All percentages are weight/weight percentages unless otherwise indicated.

DETAILED DESCRIPTION OF THE INVENTION

The piroctone compound for use in the present invention include piroctone acid, primary, secondary and tertiary olamine salts of piroctone acid (such as the diethanolamine and triethanolamine salts), and mixtures thereof, preferably piroctone acid, primary olamine salt of piroctone acid (i.e. piroctone olamine, also known as Octopirox®) and mixtures thereof.

Piroctone Olamine is an olamine salt of the hydroxamic acid derivative piroctone. It is commonly known as piroctone ethanolamine with the trade name Octopirox®.

The piroctone olamine according to the present invention is a 1:1 compound of 1-hydroxy-4-methyl-6-(2,4,4-trimethylpentyl)-2(1H)-pyridinone with 2-aminoethanol and is also designated 1-hydroxy-4-methyl-6-(2,4,4-trimethylpentyl)-2(1H) pyridinone monoethanolamine salt. The CAS number is 68890-66-4 and the compound has the general formula (I) as below:

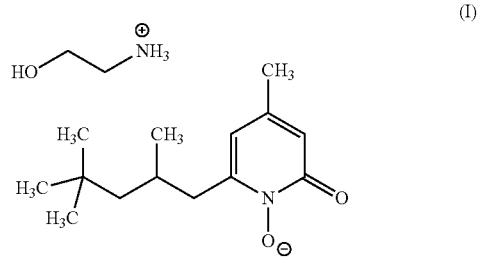

(I)

The piroctone compound, particularly the piroctone olamine is preferably present from 0.01 to 5% by weight of the total composition, more preferably from 0.1 to 5 wt %, most preferably from 0.2 to 3 wt %, of the total composition.

Compositions of the invention comprise an oil phase comprising a triglyceride oil. Preferred triglycerides comprise almond oil, coconut oil, olive oil, palm kernel oil, peanut oil and sunflower oil. Particularly preferred is coconut oil.

Compositions according to the invention comprises an oil phase. It is preferable if the oil phase forms wormlike micelles in an aqueous continuous phase. It is preferable if the oil phase is a bicontinuous phase and/or true emulsion.

Preferably the total level of non-volatile hydrocarbon oil is from 0.02 to 2 wt % of the total composition, more preferably from 0.05 to 1.0 wt %.

Compositions of the invention comprise an aliphatic fatty acid or salt thereof having a carbon chain length from $C_4$ to $C_{10}$, preferably the fatty acid or salt thereof is caprylic acid or its salt.

The weight ratio of aliphatic fatty acid to triglyceride is between 1:2 to 5:1, more preferably from 2:3 to 3:1

The composition according to the invention has a pH at 20° C. 6 or less, preferably less than 6, more preferably less than 5.5 and most preferably 5 or less. Preferably the pH at 20° C. is greater than 3.

The cosmetic composition comprises one cleansing surfactants. Surfactants are compounds which have hydrophilic and hydrophobic portions that act to reduce the surface tension of the aqueous solutions they are dissolved in. The cleansing surfactant comprises an amphoteric surfactant and an ethoxylated anionic surfactant in which the anionic surfactant preferably has an average degree of ethoxylation of less than 2.5, more preferably less than preferably less than 2, most preferably less than 1.5.

The alkyl chain of the ethoxylated anionic surfactant is preferably from 8 to 18, more preferably from 10 to 16 carbon atoms and may be unsaturated. Preferred alkyl ether sulphates are those of formula (I):

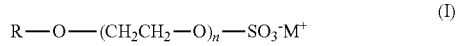

$$R—O—(CH_2CH_2—O)_n—SO_3^-M^+ \quad (I)$$

wherein R is a straight or branched alkyl chain having 8 to 18 (preferably 12 to 18) carbon atoms; n is the average degree of ethoxylation is 3 or greater, preferably 3 (and M is a solubilizing cation such as sodium, potassium, ammonium or substituted ammonium. An example is sodium lauryl ether sulphate (SLES). The most preferred example is SLES having an average degree of ethoxylation of 3 or greater, preferably an average degree of ethoxylation of 3, preferably the surfactant is sodium laureth sulphate (3EO).

Preferred amphoteric or zwitterionic cleansing surfactants including; alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Preferred amphoteric surfactants include, cocodimethyl sulphopropyl betaine, lauryl betaine, coco betaine, cocamidopropyl betaine and sodium cocoamphoacetate. A particularly preferred is amphoteric surfactant is cocamidopropyl betaine.

The ratio of ethoxylated anionic surfactant to amphoteric surfactant in which the ratio of anionic surfactant to amphoteric surfactant is less than 5:1, preferably from 2:1 to 5:1, more preferably from 3:1 to 4:1.

The total amount of cleansing surfactant in a shampoo composition for use in the invention is generally from 3 to 35 wt %, preferably from 5 to 25 wt %, most preferably from 7 to 15 wt % of the total composition.

Non-limiting examples of further cleansing anionic surfactants, which may be present but are not preferred are alkyl sulphates, alkaryl sulphonates, N-alkyl sarcosinates, alkyl phosphates, alkyl ether phosphates, acyl amino acid based surfactants, alkyl ether carboxylic acids, acyl taurates, acyl glutamates, alkyl glycinates and salts thereof, especially their sodium, magnesium, ammonium and mono-, di- and triethanolamine salts. The alkyl and acyl groups in the preceding list generally contain from 8 to 18, preferably from 10 to 16 carbon atoms and may be unsaturated.

Further non-limiting examples of cleansing surfactants may include non-ionic cleansing surfactants including; aliphatic ($C_8$-$C_{18}$) primary or secondary linear or branched chain alcohols with alkylene oxides, usually ethylene oxide and generally having from 6 to 30 ethylene oxide groups. However, it is preferred if non-ionic cleansing surfactants are not present. Other representative cleansing surfactants include mono- or di-alkyl alkanolamides (examples include coco mono-ethanolamide and coco mono-isopropanolamide) and alkyl polyglycosides (APGs). Suitable alkyl polyglycosides for use in the invention are commercially available and include for example those materials identified as: Plantapon 1200 and Plantapon 2000 ex BASF. Other sugar-derived surfactants, which can be included in compositions for use in the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

The personal care composition may comprise at least one cationic deposition polymer. Suitable cationic polymers may be homopolymers which are cationically substituted or may be formed from two or more types of monomers. The weight average ($M_w$) molecular weight of the polymers will generally be between 100 000 and 2 million daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus, when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general, secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable (non-limiting examples of) cationic polymers include:
cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
mineral acid salts of amino-alkyl esters of homo- and co-polymers of unsaturated carboxylic acids having from 3 to 5 carbon atoms, (as described in U.S. Pat. No. 4,009,256);
cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions for use in the invention include monomers of the formula:

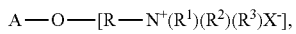

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTF A) as Polyquaternium 24. These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581). Examples of such materials include the polymer LR and JR series from Dow, generally referred to in the industry (CTFA) as Polyquaternium 10.

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C13S, JAGUAR C14 and JAGUAR C17.

Mixtures of any of the above cationic polymers may be used.

Cationic polymer will generally be present in a shampoo composition for use in the invention at levels of from 0.01 to 5%, preferably from 0.02 to 1%, more preferably from 0.05 to 0.8% by total weight of cationic polymer based on the total weight of the composition.

Preferably the composition of the invention, particularly an aqueous shampoo composition for use in the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent will generally be present in a shampoo composition for use in the invention at levels of from 0.1 to 10%, preferably from 0.15 to 6%, more preferably from 0.2 to 4% by total weight of suspending agent based on the total weight of the composition.

The cosmetic composition may optionally comprise one or more components, provided that the optional components are physically and chemically compatible with the essential components described hereinbefore, and do not otherwise unduly impair sensory, formulation rheology and conditioning performance. Individual concentrations of such optional components may range from 0.001% to 10% by weight of the total composition, preferably from 0.01% to 5% wt %. Such components may include conditioning agents, fragrance, dyes, pigments, pH adjusting agents, pearlescers or opacifiers, viscosity modifiers, preservatives, and natural hair nutrients such as botanicals, fruit extracts, sugar derivatives and amino acids.

One of the preferred optional components is a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich. Suitable cross-linked polymers of acrylic acid and acrylate esters are Pemulen TR1 or Pemulen TR2.

Mixtures of any of the above suspending agents may be used. Preferred is a mixture of cross-linked polymer of acrylic acid and crystalline long chain acyl derivative.

A most preferred example is a crosslinked polyacrylate polymer.

Suspending agent, if included, will generally be present in the composition at a level of from 0.01 to 5 wt. %, preferably from 0.1 to 2.5 wt. %, more preferably from 0.25 to 1 wt. %.

Another preferred optional component is a conditioning agent, providing conditioning benefit. Typically, the most popular conditioning agents used in cosmetic compositions are water-insoluble oily materials such as mineral oils, naturally occurring oils such as triglycerides and silicone oils. Conditioning benefit is achieved by the oily material being deposited onto the hair resulting in the formation of a film, which makes the hair more lubricated and less dry. Preferably, the conditioning agent is non-volatile, meaning that it has a vapour pressure of less than 1000 Pa at 25° C.

Preferably, the composition comprises discrete dispersed droplets of a water-insoluble conditioning agent, which has a mean droplet diameter ($D_{3,2}$) of less than 50 microns, preferably less than 30 microns, more preferably less than 15 microns, most preferably less than 10 microns. The mean droplet diameter ($D_{3,2}$) of a water-insoluble conditioning agent may be measured by means of a laser light scattering technique, for example using a 2600D Particle Sizer from Malvern Instruments. The water-insoluble conditioning agent may include non-silicone conditioning agent comprising non-silicone oily or fatty materials such as hydrocarbon oils, fatty esters and mixtures thereof. Preferably, the water-insoluble conditioning agent is emulsified silicone oil.

Suitable silicones include polydiorganosiloxanes, in particular polydimethylsiloxanes which have the CTFA designation dimethicone. Also suitable for use in compositions of this invention (particularly shampoos and conditioners) are polydimethyl siloxanes having hydroxyl end groups, which have the CTFA designation dimethiconol. Also suitable for use in compositions of this invention are silicone gums having a slight degree of cross-linking, as are described for example in WO 96/31188. Preferably, the silicone oil comprises dimethicone, dimethiconol or a mixture thereof.

The viscosity of the emulsified silicone itself (not the emulsion or the final hair care composition) is typically at least 10,000 cSt (centi-Stokes=$mm^2 \cdot S^{-1}$) at 25° C., preferably at least 60,000 cSt, most preferably at least 500,000 cSt, ideally at least 1,000,000 cSt. Preferably the viscosity does not exceed $10^9$ cSt for ease of formulation. Suitable methods for measuring the kinematic viscosity of silicone oils are known to those skilled in the art, e.g. capillary viscometers. For high viscosity silicones, a constant stress rheometer can be used to measure viscosity.

Suitable emulsified silicones for use in the compositions are available as pre-formed silicone emulsions from suppliers of silicones such as Dow Corning and GE silicones. The use of such pre-formed silicone emulsion is preferred for ease of processing and control of silicone particle size. Such pre-formed silicone emulsions will typically additionally comprise a suitable emulsifier and may be prepared by a chemical emulsification process such as emulsion polymerisation, or by mechanical emulsification using a high shear mixer.

Examples of suitable pre-formed silicone emulsions include DC1785, DC1788, DC7128, all available from Dow Corning. These are emulsions of dimethiconol/dimethicone.

Another class of silicones which may be used are functionalized silicones such as amino functional silicones, meaning a silicone containing at least one primary, secondary or tertiary amine group, or a quaternary ammonium group. Examples of suitable amino functional silicones include polysiloxanes having the CTFA designation "amodimethicone."

Preferably, silicone emulsion droplets are blended with certain types of surface active block polymers of a high molecular weight to form silicone emulsions, as described for example in WO03/094874. One preferred form of the surface active block polymer having polyoxypropylene and polyoxyethylene groups as the hydrophobic and hydrophilic part respectively has formula V and has the CTFA designation poloxamer, known commercially under the trade name "Pluronic" from BASF.

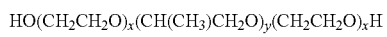
$$HO(CH_2CH_2O)_x(CH(CH_3)CH_2O)_y(CH_2CH_2O)_xH \qquad V)$$

Suitably, the mean value of x in formula I is 4 or more, preferably 8 or more, more preferably 25 or more, yet more preferably 50 or more and most preferably 80 or more. The mean value of x is typically no greater than 200. Suitably, the mean value of y is 25 or more, preferably 35 or more, more preferably 45 or more and most preferably 60 or more. The mean value of y is typically no greater than 100.

Another preferred form of the surface active block polymer is according to formula VI and has the CTFA designation Poloxamine. Those are commercially available under the trade name "Tetronic" from BASF.

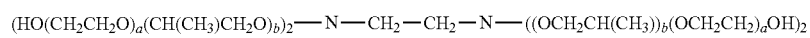
$$(HO(CH_2CH_2O)_a(CH(CH_3)CH_2O)_b)_2-N-CH_2-CH_2-N-((OCH_2CH(CH_3))_b(OCH_2CH_2)_aOH)_2 \qquad VI)$$

Suitably, the mean value of a is 2 or more, preferably 4 or more, more preferably 8 or more, even more preferably 25 or more and most preferably 40 or more. The mean value of a is typically no greater than 200. The mean value of b is suitably 6 or more, preferably 9 or more, more preferably 11 or more and most preferably 15 or more. The mean value of b is typically no greater than 50.

Preferably, the surface active block polymer is poloxamer and/or poloxamine, more preferably, the surface active block polymer is poloxamer.

Preferably, the surface active block polymer is blended with dimethicone. The weight ratio of dimethicone to surface active block polymer in the blend is preferably in the range from 2:1 to 200:1, more preferably from 5:1 to 50:1, even more preferably from 10:1 to 40:1, most preferably from 15:1 to 30:1.

The water-insoluble conditioning agent is generally present in the composition in an amount from 0.05 to 15%, preferably from 0.1 to 10%, more preferably from 0.5 to 8%, most preferably from 1 to 5%, based on the total weight of the composition and including all ranges subsumed therein.

The composition may preferably comprise a pearlescer. The preferred pearlescer is ethylene glycol ester as disclosed in U.S. Pat. No. 4,885,107, incorporated herein by reference. Preferably, the ethylene glycol ester is a mono- or, di-ester of glycol, more preferably a di-ester of glycol.

Preferably ethylene glycol mono- or di-ester is an ethylene glycol mono- or di-ester of a C12-22 fatty acid, more preferably an ethylene glycol mono- or di-ester of a saturated C12-22 fatty acid. Most preferred are the diesters comprising a mixture of palmitate and stearate. The amount of stearate should be in the range of about 10% to about 42% or in the range of about 55% to about 80% with palmitate accounting for the remainder. The amount of stearate is preferably from about 60% to about 75%, more preferably from about 80-95%, most preferably 100%. The most suitable example of a pearlescer is an ethylene glycol distearate. Pearlescer may also perform the function as a suspending agent.

The level of the ethylene glycol ester can be suitably from about 0.5% to about 6%, preferably from about 1% to about 4%, by weight of the total composition.

The viscosity of the composition s suitably ranges from 3,000 to 10,000 mPa·s, preferably from 4,000 to 8,000 mPa·s, more preferably from 5,000 to 7,000 mPa·s when measured using a Brookfield V2 viscometer (spindle RTV5, 1 minute, 20 rpm) at 30° C.

The pH of the composition of the invention preferably ranges from 3 to 9, more preferably from 4 to 8, most preferably from 4.5 to 6.5.

Rinse-off compositions are intended to be rinsed off the scalp of the user with water after use. Rinse off compositions are preferred. Leave on composition is intended not to be rinsed off the scalp of the user immediately after use (i.e. within at least the first 2 hours, preferably at least 4 hours after application of the composition). In the context of the present invention rinse-off compositions include shampoos and conditioners, as well as treatment compositions which can be left on scalp for from 0.5 minute to up to 15 minutes, preferably from 1 minute to 10 minutes, more preferably 1 minutes to 10 minutes, prior to being rinsed off.

The preferred use of the cosmetic composition is in a shampoo, particularly a rinse off shampoo. Shampoo compositions for use in the invention are generally aqueous, i.e. they have water or an aqueous solution or a lyotropic liquid crystalline phase as their major component Suitably, the shampoo composition will comprise from 50 to 98%, preferably from 60 to 92% water by weight based on the total weight of the composition. Such compositions are referred to as having an aqueous base.

The invention will now be illustrated by the following non-limiting Examples. Examples of the invention are illustrated by a number, comparative Examples by a letter, Examples Examples were prepared according to tables 1 and 3.

The deposition of the piroctone olamine was measured by thoroughly wetting with water 10 clean, dark-brown European hair switches (2.5 g/6"). 5 replicas were tested for each shampoo composition. 0.25 g shampoo was applied to one switch followed by 30 second massage. The switch was then rinsed by water for 30 seconds. 0.25 g shampoo was re-applied followed by another 30 second massage. The shampoo was then rinsed off by water for 30 seconds. The switch was allowed to dry naturally. The dried switch was extracted in 50 ml ethanol. Caution was taken not to expose the extraction to UV light. The extraction was analysed by UPLC for piroctone acid deposition.

TABLE 1

| Ingredient | A | B | C | D | E | F |
|---|---|---|---|---|---|---|
| SLES | 12 | 12 | 12 | 12 | 12 | 12 |
| CAPB | 1.6 | 1.6 | 1.6 | 1.6 | 1.6 | 1.6 |
| Caprylic Acid | 0 | 0 | 0.1 | 0.1 | 0.2 | 0.2 |
| Coconut oil | 0 | 0 | 0.25 | 0.25 | 0.25 | 0.25 |
| Piroctone Olamine | 0.5 | 0.5 | 0.5 | 0.5 | 0.5 | 0.5 |
| Water | To 100 | To 100 | To 100 | To 100 | To 100 | To 100 |
| pH | 6 | 4.5 | 6 | 4.5 | 6 | 4.5 |

TABLE 2

| Formulation | Piroctone Olamine Deposition |
|---|---|
| A | 8.64 |
| B | 9.27 |
| C | 6.04 |
| D | 9.27 |
| E | 8.08 |
| F | 9.27 |

TABLE 3

| Ingredient | G | H | I | J | 1 | 2 |
|---|---|---|---|---|---|---|
| SLES | 8.5 | 8.5 | 8.5 | 8.5 | 8.5 | 8.5 |
| CAPB | 2.3 | 2.3 | 2.3 | 2.3 | 2.3 | 2.3 |
| Caprylic Acid | 0 | 0 | 0.1 | 0.1 | 0.2 | 0.2 |
| Coconut oil | 0 | 0 | 0.25 | 0.25 | 0.25 | 0.25 |
| Piroctone Olamine | 0.5 | 0.5 | 0.5 | 0.5 | 0.5 | 0.5 |
| Water | To 100 | To 100 | To 100 | To 100 | To 100 | To 100 |
| pH | 6 | 4.5 | 6 | 4.5 | 6 | 4.5 |

TABLE 4

| Formulation | Piroctone Olamine Deposition (ppm) |
|---|---|
| G | 8.88 |
| H | 7.5 |
| I | 7.75 |
| J | 9.69 |
| 1 | 10.12 |
| 2 | 13.05 |

The invention claimed is:

1. A personal cleansing composition comprising:
i) a cleansing surfactant consisting of an amphoteric surfactant and an anionic surfactant which if ethoxylated has a degree of ethoxylation of less than 3, wherein a ratio of the anionic surfactant to the amphoteric surfactant is less than 5:1;
ii) an oil phase comprising at least one triglyceride oil, consisting of coconut oil;
iii) caprylic acid or salt thereof; and
iv) a piroctone compound;

wherein the composition has a pH of 6 or less at 20° C., and a weight ratio of caprylic acid to triglyceride oil is 1:1.25.

2. The personal cleansing composition according to claim 1, wherein the pH of the composition is less than 6.

3. The personal cleansing composition according to claim 1, wherein the oil phase forms wormlike micelles in an aqueous continuous phase.

4. The personal cleansing composition according to claim 1, wherein the cleansing surfactant is an ethoxylated alkyl sulphate having a degree of ethoxylation of less than 2.

5. The personal cleansing composition according to claim 4, wherein the ethoxylated alkyl sulphate is sodium laureth sulphate (1EO).

6. The personal cleansing composition according to claim 1, wherein the piroctone compound is piroctone olamine.

7. The personal cleansing composition according to claim 1, further comprising a cationic polymer.

8. The personal cleansing composition according to claim 1, wherein the cleansing surfactant is present in an amount from 3 to 35 wt %.

9. The personal cleansing composition according to claim 1, wherein the piroctone compound is present in an amount from 0.1 to 5 wt %.

10. The personal cleansing composition according to claim 1, wherein the triglyceride oil is present in an amount from 0.05 to 1.0 wt % of the total composition.

11. The personal cleansing composition according to claim 1, wherein the personal cleansing composition is a shampoo.

12. A non-therapeutic method of treating hair or scalp, comprising applying a personal cleansing composition according to claim 1 to the hair or scalp.

13. The non-therapeutic method according claim 12, wherein the personal cleansing composition is washed off after use.

14. A method for mitigating dandruff, comprising applying a personal cleansing composition according to claim 1 to hair or scalp.

15. The personal cleansing composition according to claim 2, wherein the pH of the composition is less than 5.5.

16. The personal cleansing composition according to claim 8, comprising a total cleansing surfactant level of from 5 to 25 wt % of the total composition.

17. The personal cleansing composition according to claim 8, comprising a total cleansing surfactant level of from 7 to 15 wt % of the total composition.

18. The personal cleansing composition according to claim 9, wherein the piroctone compound is present in an amount from 0.2 to 3 wt % of the total composition.

19. A personal cleansing composition consisting of:
i) a cleansing surfactant comprising an amphoteric surfactant and an anionic surfactant which if ethoxylated has a degree of ethoxylation of less than 3, wherein a ratio of the anionic surfactant to the amphoteric surfactant is less than 5:1;
ii) an oil phase comprising at least one triglyceride oil consisting of coconut oil;
iii) an aliphatic fatty acid or salt thereof having a carbon chain length from $C_4$ to $C_{10}$;
iv) a piroctone compound;
v) optionally a cationic deposition polymer;
vi) optionally a non-ionic cleansing surfactant;
vii) optionally a suspending agent;
viii) optionally one or more of conditioning agent, fragrance, dye, pigment, pH adjusting agent, pearlescers, opacifier, viscosity modifier, preservative, or natural hair nutrient; and
ix) water;

wherein the composition has a pH of 6 or less at 20° C., and a weight ratio of aliphatic fatty acid to triglyceride oil is 1:1.25.

20. A personal cleansing composition comprising:
i) from 3 to 35 wt % of a cleansing surfactant consisting of an amphoteric surfactant and an anionic surfactant which if ethoxylated has a degree of ethoxylation of less than 3, wherein a ratio of the anionic surfactant to the amphoteric surfactant is less than 5:1;
ii) from 0.02 to 2 wt % of an oil phase comprising at least one triglyceride oil, consisting of coconut oil;
iii) caprylic acid or salt thereof; and
iv) from 0.01 to 5 wt % of a piroctone compound;

wherein the composition has a pH of 6 or less at 20° C., and a weight ratio of caprylic acid to triglyceride oil is 1:1.25.

* * * * *